(12) United States Patent
Fritz et al.

(10) Patent No.: US 10,246,394 B2
(45) Date of Patent: Apr. 2, 2019

(54) SEPARATION PROCESSING METHOD FOR A PRODUCT STREAM OF A DIMETHYL ETHER REACTOR

(71) Applicant: Linde Aktiengesellschaft, München (DE)

(72) Inventors: Helmut Fritz, München (DE); Andreas Peschel, Wolfratshausen (DE)

(73) Assignee: LINDE AKTIENGESELLSCHAFT, München (DE)

( * ) Notice: Subject to any disclaimer, the term of this patent is extended or adjusted under 35 U.S.C. 154(b) by 378 days.

(21) Appl. No.: 15/109,951

(22) PCT Filed: Jan. 5, 2015

(86) PCT No.: PCT/EP2015/050046
§ 371 (c)(1),
(2) Date: Jul. 6, 2016

(87) PCT Pub. No.: WO2015/104238
PCT Pub. Date: Jul. 16, 2015

(65) Prior Publication Data
US 2016/0332945 A1 Nov. 17, 2016

(30) Foreign Application Priority Data
Jan. 7, 2014 (EP) .................................. 14000041

(51) Int. Cl.
*B01D 3/14* (2006.01)
*B01D 53/14* (2006.01)
(Continued)

(52) U.S. Cl.
CPC .............. *C07C 41/42* (2013.01); *B01D 3/143* (2013.01); *B01D 53/1493* (2013.01);
(Continued)

(58) Field of Classification Search
CPC ....... C07C 43/043; C07C 41/40; C07C 41/42; B01D 2257/108; B01D 2257/502;
(Continued)

(56) References Cited

U.S. PATENT DOCUMENTS

| 4,536,485 A | 8/1985 | Topp-Jorgensen |
| 5,189,203 A | 2/1993 | Hansen et al. |

(Continued)

FOREIGN PATENT DOCUMENTS

| DE | 19943219 A1 | 3/2001 |
| EA | 020097 B1 | 8/2014 |

(Continued)

OTHER PUBLICATIONS

Taiwan Patent Application No. 103144500 Office Action dated Aug. 14, 2018, 3 pages.
(Continued)

*Primary Examiner* — Cabrena Holecek
(74) *Attorney, Agent, or Firm* — Lathrop Gage LLP (57) ABSTRACT

A method for the processing, by separation technology, of a product stream (g), containing at least dimethyl ether, methanol, water, carbon dioxide, carbon monoxide and hydrogen, from a reactor (4) used for the synthesis of dimethyl ether (z) from synthesis gas (e), is proposed. The product stream (g) is fed, in at least partially gaseous form, into an absorption column (6) operated with a liquid reflux, a gaseous top stream (m) being removed from the absorption column (6) at the top and a liquid sump stream (p) being removed at the bottom. The sump stream (p) is at least partially fed into a first distillation column (5), a gaseous transfer stream (q) containing dimethyl ether and a stream (r) predominantly containing methanol and/or water being removed from the first distillation column (5). The top stream (m) is at least partially cooled initially to a first
(Continued)

temperature level and subsequently further cooled to one or more further temperature levels, a first condensate stream (n) being formed after the cooling to the first temperature level and one or more further condensate streams (s, t) being formed after the further cooling to the further temperature level or levels. The first condensate stream (n) is partially used to form the liquid reflux and the further condensate stream or streams (s, t) is or are at least partially fed into a further distillation column (9), from which a liquid stream (z) predominantly containing dimethyl ether and poor in or free from carbon dioxide is removed at the bottom. The invention also relates to a corresponding separation apparatus and an apparatus (100) for producing dimethyl ether.

11 Claims, 2 Drawing Sheets (51) Int. Cl.
    *C07C 41/42*     (2006.01)
    *C07C 41/40*     (2006.01)

(52) U.S. Cl.
    CPC ........ *C07C 41/40* (2013.01); *B01D 2257/108* (2013.01); *B01D 2257/502* (2013.01); *B01D 2257/504* (2013.01); *B01D 2257/80* (2013.01); *Y02A 50/2341* (2018.01); *Y02C 10/06* (2013.01); *Y02P 20/152* (2015.11); *Y02P 70/34* (2015.11)

(58) Field of Classification Search
    CPC .......... B01D 2257/504; B01D 2257/80; B01D 3/143; B01D 53/1493; Y02A 50/2341; Y02C 10/06; Y02P 20/152; Y02P 70/34

See application file for complete search history.

(56) References Cited

U.S. PATENT DOCUMENTS

| | | |
|---|---|---|
| 5,685,170 A | 11/1997 | Sorensen |
| 2013/0327086 A1* | 12/2013 | Moussa ................ B01D 3/14 |
| | | 62/617 |

FOREIGN PATENT DOCUMENTS

| | | |
|---|---|---|
| EP | 0343454 A2 | 11/1989 |
| RU | 2256645 C2 | 7/2005 |
| RU | 2572557 C2 | 1/2016 |
| WO | WO 01/17937 A1 | 3/2001 |

OTHER PUBLICATIONS

Russian Patent Application No. 2016127563/05 English translation of Search Report, dated Aug. 7, 2018, 2 pages.
Chinese Patent Application No. 201580003641.5 First Office Action dated Jun. 7, 2018, 7 pages.
Chinese Patent Application No. 201580003641.5 English translation of First Office Action dated Jun. 7, 2018, 9 pages.
PCT/EP2015/050046 English Translation of the International Search Report & Written Opinion dated Mar. 11, 2015, 11 pages.

* cited by examiner

SEPARATION PROCESSING METHOD FOR A PRODUCT STREAM OF A DIMETHYL ETHER REACTOR

The invention relates to a method for the processing by separation technology of a product stream containing at least dimethyl ether, methanol, water, carbon dioxide, carbon monoxide and hydrogen, from a reactor which is used for synthesising dimethyl ether from synthesis gas, a corresponding separation apparatus and an apparatus for producing dimethyl ether according to the pre-characterising clauses of the independent claims.

PRIOR ART

Dimethyl ether (DME) is the structurally simplest ether. Dimethyl ether contains two methyl groups as organic radicals. Dimethyl ether is polar and is conventionally used in liquid form as a solvent. Dimethyl ether can also be used as a refrigerant and replace conventional chlorofluorocarbons.

Recently, dimethyl ether has increasingly been used as a substitute for fuel gas (liquid gas) and conventional fuels such as diesel. Because of its comparatively high cetane number of 55 to 60, conventional diesel engines, for example, need to be only slightly modified in order to run on dimethyl ether. Dimethyl ether burns comparatively cleanly without forming carbon deposits. If dimethyl ether is produced from biomass, it counts as a so-called biofuel and can therefore be marketed on favourable tax terms.

Dimethyl ether can be produced either directly from methanol or indirectly from natural or bio gas. In the latter case, the natural or bio gas is first of all reformed into synthesis gas. Synthesis gas can also be obtained by other methods, for example by pyrolysis of waste materials or biomass. The synthesis gas is then either converted into methanol and then into dimethyl ether in a two-step reaction or converted directly into dimethyl ether in a one-step reaction.

The synthesis of dimethyl ether from synthesis gas has thermodynamic and economic advantages over synthesis from methanol.

The present invention relates in particular to the one-step synthesis of dimethyl ether, the term "one-step" synthesis referring to a method of synthesis in which all the reactions take place in one and the same reactor. The one-step synthesis of dimethyl ether is known for example from U.S. Pat. No. 4,536,485 A and U.S. Pat. No. 5,189,203 A. Conventionally, hybrid catalysts are used. The reaction is exothermic and is typically carried out at a temperature of from 200 to 300° C. at a pressure of 20 to 100 bar.

For the one-step synthesis of dimethyl ether, normally upright tube reactors are used which are charged from below with pressurised, heated synthesis gas. A product stream obtained in the tube reactor is removed from the top, cooled and introduced into a separation.

The product stream contains, in addition to dimethyl ether, unreacted components of the synthesis gas as well as other reaction products. Typically, the product stream comprises, besides dimethyl ether, at least methanol, water, carbon dioxide, carbon monoxide and hydrogen and minor amounts of methane, ethane, organic acids and higher alcohols.

The product stream is obtained at the above-mentioned pressure of between 20 and 80 bar. In order to obtain dimethyl ether from the product stream the latter has to be cooled to temperatures significantly below 0° C. In order to prevent the water from freezing and/or to obtain dimethyl ether according to a relevant specification it may be necessary to separate off fairly large amounts of methanol and/or water before the product stream is cooled.

Because of the comparatively high solubility of dimethyl ether and carbon dioxide in methanol and water and the high pressure, however, satisfactory separation cannot be achieved by one-step partial condensation in spite of the considerable differences in the boiling points of the above-mentioned components.

From US 2013/327086 A1 a method is known for easier separation of a reaction product from a reaction gas mixture, consisting of the reaction product, at least one low boiler and/or non-condensable reaction gas and at least one high boiler. EP 0 343 454 A2 relates to a method integrated in a methanol synthesis for preparing dimethyl ether by catalytic dehydration of methanol and purifying the dehydration product by feeding it into a distillation column in order to recover pure dimethyl ether. To increase the yield of propane, butane and other heavy components from a natural gas stream, U.S. Pat. No. 5,685,170 A proposes the use of an absorption column. A method for preparing dimethyl ether is also known from DE 199 43 219 A1, for example.

There is a need for improved options for reducing the methanol and/or water content of a corresponding product stream, particularly at the pressure mentioned hereinbefore.

DISCLOSURE OF THE INVENTION

Against this background the present invention proposes a method of processing, by separation technology, a product stream containing at least dimethyl ether, methanol, water, carbon dioxide, carbon monoxide and hydrogen, from a reactor which is used for synthesising dimethyl ether from synthesis gas, a corresponding separation apparatus and an apparatus for producing dimethyl ether according to the features of the independent claims. Preferred embodiments are recited in the sub-claims and the description that follows.

Before the explanation of the features and advantages of the present invention, their basis and the terminology used will be explained.

Liquid and gaseous streams in the terminology used here may be rich or poor in one or more components, "rich" denoting a content of at least 90%, 95%, 99%, 99.5%, 99.9%, 99.99% or 99.999% and "poor" denoting a content of not more than 10%, 5%, 1%, 0.1%, 0.01% or 0.001%, on a molar, weight or volume basis. Liquid and gaseous streams in the terminology used here may also be enriched in or depleted in one or more components, these terms referring to a corresponding content in a starting mixture from which the liquid or gaseous stream has been obtained. The liquid or gaseous stream is "enriched" if it contains at least 1.1 times, 1.5 times, 2 times, 5 times, 10 times, 100 times or 1,000 times the amount, and "depleted" if it contains not more than 0.9 times, 0.5 times, 0.1 times, 0.01 times or 0.001 times the amount of a corresponding component, based on the starting mixture.

A liquid or gaseous stream is "derived" from another liquid or gaseous stream (which is also referred to as the starting stream) if it comprises at least some components that were present in the starting stream or obtained therefrom. A stream which is derived in this way may be obtained from the starting stream by separating off or deriving a partial stream or one or more components, concentrating or depleting one or more components, chemically or physically reacting one or more components, heating, cooling, pressurising and the like.

The present application uses the terms "pressure level" and "temperature level" to characterise pressures and temperatures, the intention being to indicate that corresponding pressures and temperatures in a corresponding apparatus do not have to be used in the form of precise pressure or temperature values in order to implement the inventive concept. However, such pressures and temperatures typically vary within certain ranges which are for example ±1%, 5%, 10%, 20% or even 50% either side of a mean value. Corresponding pressure levels and temperature levels may be located in disjointed ranges or in ranges that overlap. In particular, pressure levels will include, for example, unavoidable or expected pressure losses caused, for example, by the effects of cooling. The same is true of temperature levels. The pressure levels given in bar are absolute pressures.

A "distillation column" in the terminology used here is a separating unit which is arranged to at least partially separate a mixture of substances (fluid) prepared in gaseous or liquid form or in the form of a two-phase mixture with liquid and gaseous components, optionally also in the supercritical state, i.e. to produce, from the mixture of substances, pure substances or mixtures of substances which are enriched or depleted in at least one component compared with the mixture of substances, in the sense described above. Distillation columns are sufficiently known from the field of separation technology. Typically, distillation columns are configured as cylindrical metal containers which are equipped with fittings such as perforated plates or structured or unstructured packing. A distillation column is characterised inter alia in that a liquid fraction separates off at the bottom, also referred to as the sump. This liquid fraction, which is also referred to as the sump product, is heated in a distillation column by means of a sump evaporator so that some of the sump liquid is continuously evaporated and rises in gaseous form within the distillation column. A distillation column is also typically provided with a so-called top condenser into which at least some of a gas mixture that is to be enriched in an upper part of the distillation column or a corresponding pure gas, also referred to as the top gas, is fed, liquefied and added at the top of the distillation column as a liquid reflux.

In contrast to a distillation column, an "absorption column" does not have a sump evaporator. Absorption columns are also generally known from the field of separation technology. Absorption columns are used for absorption in the phase counterflow and are therefore also referred to as counterflow columns. In counterflow absorption, the releasing gas phase flows upwards through an absorption column. The receiving solution phase, added at the top and drawn off at the bottom, flows counter to the gas phase. In a corresponding absorption column, fittings are also typically provided which ensure a stepwise phase contact (plates, spray zones, rotating plates, etc.) or constant phase contact (unregulated pouring of fillings, packings, etc.).

For the design and specific configuration of distillation columns and absorption columns reference is made to textbooks on the subject (cf. for example Sattler, K.: Thermische Trennverfahren: Grundlagen, Auslegung, Apparate, [Thermal separation methods: Principles, Design, Apparatus], $3^{rd}$ edition 2001, Weinheim, Wiley-VCH).

Where reference is hereinafter made to a "synthesis" of dimethyl ether for short, this denotes a method in which a feed containing a synthesis gas, i.e. a gas mixture, which contains at least carbon monoxide and hydrogen in suitable amounts, is reacted to form a corresponding product stream containing dimethyl ether. Because of the incomplete reaction and because of the occurrence of secondary reactions during the synthesis of dimethyl ether, particularly depending on the characteristics of the catalysts used and the respective amounts of the components of the synthesis gas, a corresponding product stream contains not only dimethyl ether but also other compounds. These are, at least, methanol, water, carbon dioxide, carbon monoxide and hydrogen but also, typically, minor amounts of methane, ethane, organic acids and higher alcohols. These additional compounds have to be separated off, as mentioned above. The separation is carried out on the one hand to enable subsequent separation steps and on the other hand to recover dimethyl ether with the required purity, i.e. "in accordance with the specifications".

Advantages of the Invention

The present invention starts from the problem described hereinbefore, namely that, as already explained, in order to separate dimethyl ether from a product stream from a reactor for the preparation of dimethyl ether, conventionally, the latter has to be cooled to temperatures significantly below 0° C. To avoid water freezing out and/or to enable dimethyl ether to be obtained according to the specification, fairly large amounts of methanol and water have to be separated off. This proves to be a complicated operation as dimethyl ether and carbon dioxide dissolve rather well in methanol and water and at the high pressures used it is not possible to achieve satisfactory separation with one-step partial condensation, in spite of the differences in boiling point. Reducing the pressure to lower pressures such as ambient pressure, for example, which would make separation easier, is disadvantageous, as a correspondingly high pressure of between 20 and 100 bar is needed again for the subsequent separation under low temperature conditions. Therefore, energy-consuming recompression would have to take place. However, even multi-step condensation on its own does not lead to satisfactory separation.

Against this background, the present invention proposes a method for the processing, by separation technology, of a corresponding product stream which contains at least dimethyl ether, methanol, water, carbon dioxide, carbon monoxide and hydrogen. As already mentioned, a product stream of this kind comes from a reactor used for the synthesis of dimethyl ether from synthesis gas, particularly a tube reactor which is supplied with synthesis gas and is designed for the one-step synthesis of dimethyl ether or the at least partial reaction of synthesis gas to form dimethyl ether.

According to the invention it is envisaged that the product stream should be fed, at least partially in gaseous form, into an absorption column operated with a liquid reflux. Thus, when introduced in a completely gaseous form, it is fed in above the dew point of the corresponding product stream or the component with the highest boiling point at the pressure level used. However, a partially liquid product stream may also be fed into the absorption column, i.e. the product stream may also be "partially condensed".

A gaseous top stream is removed from the top of the absorption column while a liquid sump stream is removed from the bottom. Even when a partially liquid stream is fed in, gases such as carbon dioxide, carbon monoxide and hydrogen scarcely go over into the sump stream as the temperatures used in the absorption column are comparatively high. Advantageously, the entry temperature into the absorption column is substantially higher than the temperature at its top (the latter is typically at a temperature level of from 50 to 150° C.). As a result, substantially less of the gases dissolve in the sump stream than would be the case in a one-step condensation, for example. The sump stream is therefore poor in or free from the abovementioned gases in both cases, thus significantly improving the separation in the steps described hereinafter.

The top stream is at least partially cooled first of all to a first temperature level and then further cooled to one or more further temperature levels, a first condensate stream being formed after the cooling to the first temperature level and one or more further condensate streams being formed after the cooling to the further temperature level or levels. The further cooling can thus be in several steps and optionally after a final cooling step a further absorption column may be used, as explained hereinafter. After the other cooling steps, however, typically normal separation containers are used to form the condensate streams. If it is stated that "the top stream" (or a part thereof) is cooled repeatedly, forming condensates, it will be understood that each additional cooling step only relates to the uncondensed fraction (or a part thereof), i.e. the quantity of fluid cooled decreases continuously.

The sump stream from the absorption column is at least partly fed into a first distillation column, while a transfer stream containing dimethyl ether and a stream containing predominantly methanol and/or water are removed from the first distillation column. The "transfer stream" is typically formed from fluid which is drawn off from the top of the first distillation column.

The transfer stream may be liquid, partly liquid or gaseous. For example, to provide a liquid reflux, fluid may be drawn off from the first distillation column and partly liquefied in a top condenser. The transfer stream may be a corresponding fluid which is not liquefied (or a part thereof), but may also be correspondingly liquefied or partially liquefied fluid. The transfer stream thus typically also contains carbon dioxide in addition to dimethyl ether, but is preferably poor in or free from water and/or methanol. Its further treatment is described hereinafter.

On account of the measures proposed according to the invention the stream predominantly containing methanol and/or water which is also drawn off from the distillation column is not fed into the low temperature separation in which water and/or methanol could cause problems, as already stated.

At least part of the other condensate stream or streams and the transfer stream is fed into a further distillation column from which a liquid stream is removed at the sump end, this liquid stream predominantly containing dimethyl ether and being poor in or free from carbon dioxide. This is the actual product of the method according to the invention.

According to the invention the first condensate stream is used partly to form the liquid reflux and partly for other purposes. If it is free from water and optionally methanol the fraction of the first condensate stream which is not used to form the liquid reflux may be at least partially fed into the further distillation column into which at least part of the other condensate stream or streams and the transfer stream is fed. Otherwise, the fraction of the first condensate stream which is not used to form the liquid reflux may also be fed into the first distillation column into which the liquid sump stream from the absorption column is also fed.

In other words, within the scope of the present invention, the absorption column is operated with a liquid reflux which is formed, according to the invention, from a condensate stream which is separated off in liquid form from the gaseous top stream removed at the top of the absorption column after cooling to a first temperature level. The top stream is the purification product of the absorption column which has previously passed through the absorption column from the bottom to the top in counterflow with the liquid reflux.

If the first distillation column is operated at a higher pressure than the further distillation column, the transfer stream is advantageously supplied from the first distillation column in gaseous or liquid form and can be transferred directly into the other distillation column. If, on the other hand, the first distillation column is operated at a lower pressure than the further distillation column, a liquid transfer stream which can be put under higher pressure by means of a pump is advantageously used. In this case, a gaseous stream consisting of fluid from the transfer stream may be left, and this may be piped to a burner, for example. Typically it is a small amount compared to the liquid condensate stream which is transferred into the other distillation column. The pressures used and the first and further distillation columns are advantageously selected such that in the first distillation column cooling water can be used where possible as the cooling medium in the top condenser and in the other distillation column it is possible to carry out effective separation of carbon dioxide and dimethyl ether using a coolant at a temperature of more than about −47° C. (above the freezing point of carbon dioxide). The operating pressures of both distillation columns are below that at which the condensate or further condensate(s) is or are formed. Thus the separating problem described above is solved within the scope of the present invention, inter alia, in that the product stream is first passed into an absorption column and washed with at least some of the condensate obtained from a first condensation step as reflux. The gaseous top stream of the absorption column is fed into the first condensation stage. The temperature of the condensation in this first condensation stage, i.e. the first temperature level at which the condensate stream is separated off, depends on the dew point of the top stream or its components and the refrigerants available, such as air, cooling water, C3 refrigerant or dimethyl ether. Any dimethyl ether getting into the reflux of the absorption column and hence the sump stream is not lost, according to the invention, but is at least for the most part transferred, in the transfer stream from the first distillation column into which the sump stream is fed beforehand, into the further distillation column which serves to provide the actual dimethyl ether product. At the same time, as already mentioned, the present invention allows low temperature separation with no adverse effects of water and/or methanol in the product stream, as these components are washed out in the absorption column.

The method proposed according to the invention proves more favourable than conventional methods in terms of energy consumption, with the result that the measures according to the invention allow advantageous separation compared with separation methods known from the prior art.

Advantageously, the absorption column is operated, particularly by adjustment of the temperature and pressure conditions and the quantity of reflux used, such that the top stream is low in methanol and/or water. Preferably, this top stream is substantially free from methanol and/or water.

The top stream thus still essentially contains the other components of the product stream, namely at least dimethyl ether, carbon dioxide, carbon monoxide and hydrogen. A stream with this composition proves unproblematic in the downstream separating units as, in particular, it no longer contains any water that might possibly freeze out or methanol that might have a negative effect on the separation properties.

According to the invention it is envisaged, as already mentioned, that a fraction of the top stream from the absorption column which has remained in gaseous form at the first temperature level should be cooled successively to at least one other temperature level, for example to a second and a third temperature level. At the second and third temperature levels, additional condensate streams may be separated off in liquid form. Thus, after corresponding cooling, one or more further condensations are carried out. Stepwise cooling has proved particularly favourable in terms of energy consumption and is known for example from the separation of ethane from ethane-containing mixtures.

Advantageously, in the separation of corresponding further condensate streams, the temperature levels used are selected such that these further condensate streams are low in carbon monoxide and hydrogen. Advantageously, these condensate streams thus essentially still contain carbon dioxide and dimethyl ether which can be separated from one another in a subsequent separation.

The invention provides, for this purpose, the further distillation column into which, optionally, the fraction of the condensate stream not used as a liquid reflux (see above) which is separated from the gaseous top stream from the absorption column, and in any case at least one of the other condensate streams and the transfer stream, is at least partially fed. The condensates obtained in the other condensation steps and optionally other fluids fed in are separated in this further distillation column.

This is carried out under conditions which ensure that a liquid sump stream which is rich in dimethyl ether and poor in carbon dioxide can be removed from the bottom of the further distillation column. The separating function of the further distillation column can thus be described as performing the separation of carbon dioxide and dimethyl ether in a corresponding mixture. A gaseous top stream which is rich in carbon dioxide and poor in dimethyl ether is removed from the top of the further distillation column.

The present invention is particularly suitable for methods in which the product stream from the reactor used for the synthesis of dimethyl ether from synthesis gas is fed into the absorption column at a pressure level of 20 to 100 bar, particularly at a pressure level of 30 to 80 bar. The separation of methanol and/or water can be carried out under pressure, with no need for any pressure release beforehand which would then require a new build-up of pressure, with the associated high energy costs.

The present invention is suitable for separation immediately after the synthesis and subsequent cooling. It is particularly advantageous if the cooling is only carried out by a heat exchange of the product stream with a synthesis gas stream fed into the reactor or reactors, so that there is no need for any additional expensive cooling equipment with coolants that probably must be externally supplied. This is possible because within the scope of the invention the dew point of the product stream must not be underrun. Thus, in spite of the cooling, the product stream may remain in a superheated state, i.e. at a temperature level above the dew point. Its temperature level when fed into the absorption column may thus be, for example, 60 to 150° C., particularly 70 to 120° C., for example 80 to 100° C. or, in relation to the dew point, for example, at least 10° C. and not more than 30 to 50° C. above the dew point. As already mentioned, the product may be introduced in partially condensed form.

The ensuing successive cooling of the top stream of the absorption column takes place at progressively lower temperatures, advantageously down to a minimum temperature level which is between the melting temperature of carbon dioxide at the pressure level used and −15° C., for example at −50 to −20° C. and particularly at about −35° C., the temperature of a C3 refrigerant. The temperature level may also be just above, i.e. at least 0.5 to 10° C., particularly 1 to 5° C. above the melting temperature of carbon dioxide at the pressure level used. The temperature level used also depends on the composition of the top stream and the desired composition of the condensates thus obtained. In this way it is possible to achieve virtually total separation of the carbon dioxide and dimethyl ether from the top stream of the absorption column.

After cooling to the minimum temperature level, a fraction of the top stream which remains in gaseous form can be fed into a further absorption column which allows particularly effective depletion of dimethyl ether. For this purpose the further absorption column may be operated with another liquid reflux which is formed from a liquefied, carbon dioxide-rich top stream from the further distillation column.

The method according to the invention may be used with product streams of many compositions. Corresponding product streams contain, for example, 2 to 50 mol %, particularly 5 to 30 mol %, of dimethyl ether, 0.1 to 20 mol %, particularly 0.7 to 10 mol %, of methanol, 0.1 to 20 mol %, particularly 0.8 to 10 mol %, of water, 1 to 50 mol %, particularly 3 to 30 mol %, of carbon dioxide, 0.1 to 25 mol %, particularly 1 to 11 mol % of carbon monoxide and 5 to 90 mol %, particularly 20 to 80 mol %, of hydrogen. After the elimination of water and methanol, the gas mixture is preferably poor in water and methanol.

Such product streams are obtained for example by charging a reactor with a synthesis gas in which the ratio of hydrogen to carbon monoxide is 0.8 to 8 mol/mol, particularly 1 to 6 mol/mol.

A separation apparatus which is designed for processing, by separation technology, a product stream from a reactor used for the synthesis of dimethyl ether from synthesis gas, is also a subject of the present invention and is recited in the corresponding independent claim.

A separation apparatus of this kind is designed particularly for carrying out a method as explained hereinbefore.

A corresponding separation apparatus, as well as an apparatus provided according to the invention for the preparation of dimethyl ether, benefits from the advantages described above, to which reference is therefore be expressly made.

The invention is described in more detail with reference to the drawings, which show an embodiment of the invention compared with the prior art.

BRIEF DESCRIPTION OF THE DRAWINGS

In the Figures, corresponding elements have been given identical reference numerals and have not been repeatedly described, in the interests of clarity.

DETAILED DESCRIPTION OF THE DRAWINGS

Figure 1:
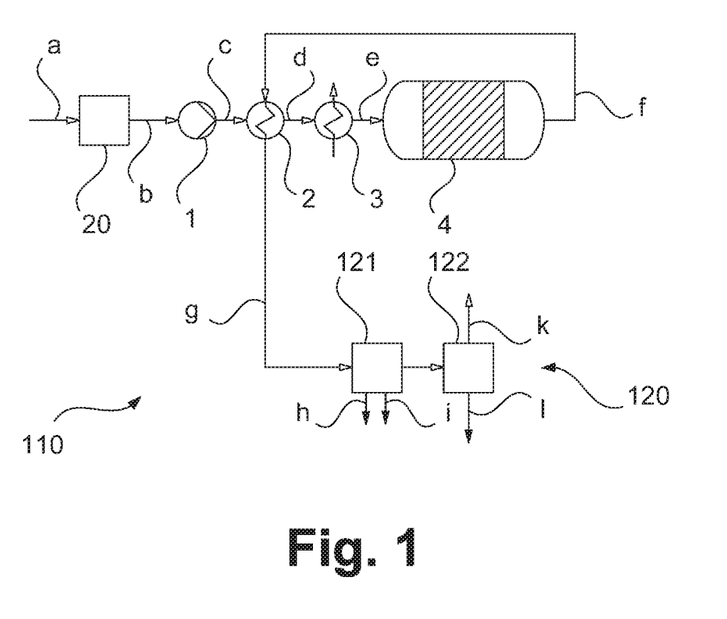
FIG. 1 shows an apparatus for the production of dimethyl ether according to the prior art, in schematic representation.

FIG. 1 schematically shows an apparatus for producing dimethyl ether according to the prior art which is generally designated 110.

The apparatus 110 encompasses a synthesis gas reactor 20, shown in highly schematic representation, which can be charged with a suitable feed a, for example natural or bio gas. A synthesis gas stream b can be removed from the synthesis gas reactor 20.

The synthesis gas stream b can be increased to a higher pressure by means of a compressor 1, optionally after further streams have been mixed therewith. A pressure as required for a subsequent one-step synthesis of dimethyl ether, for example a pressure of 20 to 100 bar, can be obtained thereby.

A correspondingly compressed stream, now designated c, is passed through a first heat exchanger 2 which can be heated with a product stream f from a reactor 4 for the synthesis of dimethyl ether (see below). The correspondingly heated stream d has a temperature of 200 to 300° C., for example, downstream of the first heat exchanger 2. The stream d is optionally passed through a second heat exchanger 3, which is also referred to as a peak heater.

The stream e which is heated further in the second heat exchanger 3 is fed into the reactor 4, which is embodied as a tube reactor and the reaction tubes of which are filled with a suitable catalyst for the one-step synthesis of dimethyl ether. The representation in FIG. 1 is highly simplified. Typically, reactors 4 for the synthesis of dimethyl ether are arranged vertically, a stream e being fed into the tube reactor 4 at the bottom. A stream f is removed from the reactor 4 at the top.

Because of the exothermic reaction in the tube reactor 4, the stream f is present at an even higher temperature. The stream f, acting as a heating medium, is passed through the heat exchanger 2. It is thus cooled to a temperature which is, for example, about 30° C. above the temperature of the compressed stream c. The correspondingly cooled stream, now designated g, is supplied to a conventional separation apparatus 120. In the separation apparatus 120, a methanol stream h and a water stream i are separated off from the stream g in one step 121, for example, with intermediate processes of depressurisation, cooling, re-pressurisation, etc. (not shown). From the residue remaining, in a step 122, the streams k and l are formed, which may be a stream k rich in carbon dioxide and a stream l rich in dimethyl ether.

The composition of the streams k and l depends on the composition of the stream g and the operating parameters of the separation apparatus 120. As already explained, in spite of the large differences in boiling point between the components involved, it is not possible to achieve satisfactory separation by one-step partial condensation because of the good solubility of dimethyl ether and carbon dioxide in methanol/water at the high pressure used.

If further purification is to be carried out in subsequent separation steps, cooling to temperatures significantly below 0° C. has to be carried out. This is not possible, however, when the stream i has a corresponding water content, as the water would freeze out. Satisfactory separation would not be possible if methanol were present. The presence of methanol without water ("dry methanol") is to be avoided as this would damage the heat exchangers used.

This also applies if it is necessary to cool the stream l, which is initially present only in an unsatisfactorily separated state.

Against this background the present invention proposes, as already explained, that a product stream, in the case the stream g, be introduced into an absorption column at a temperature above the dew point and be separated in said column.

Figure 2:
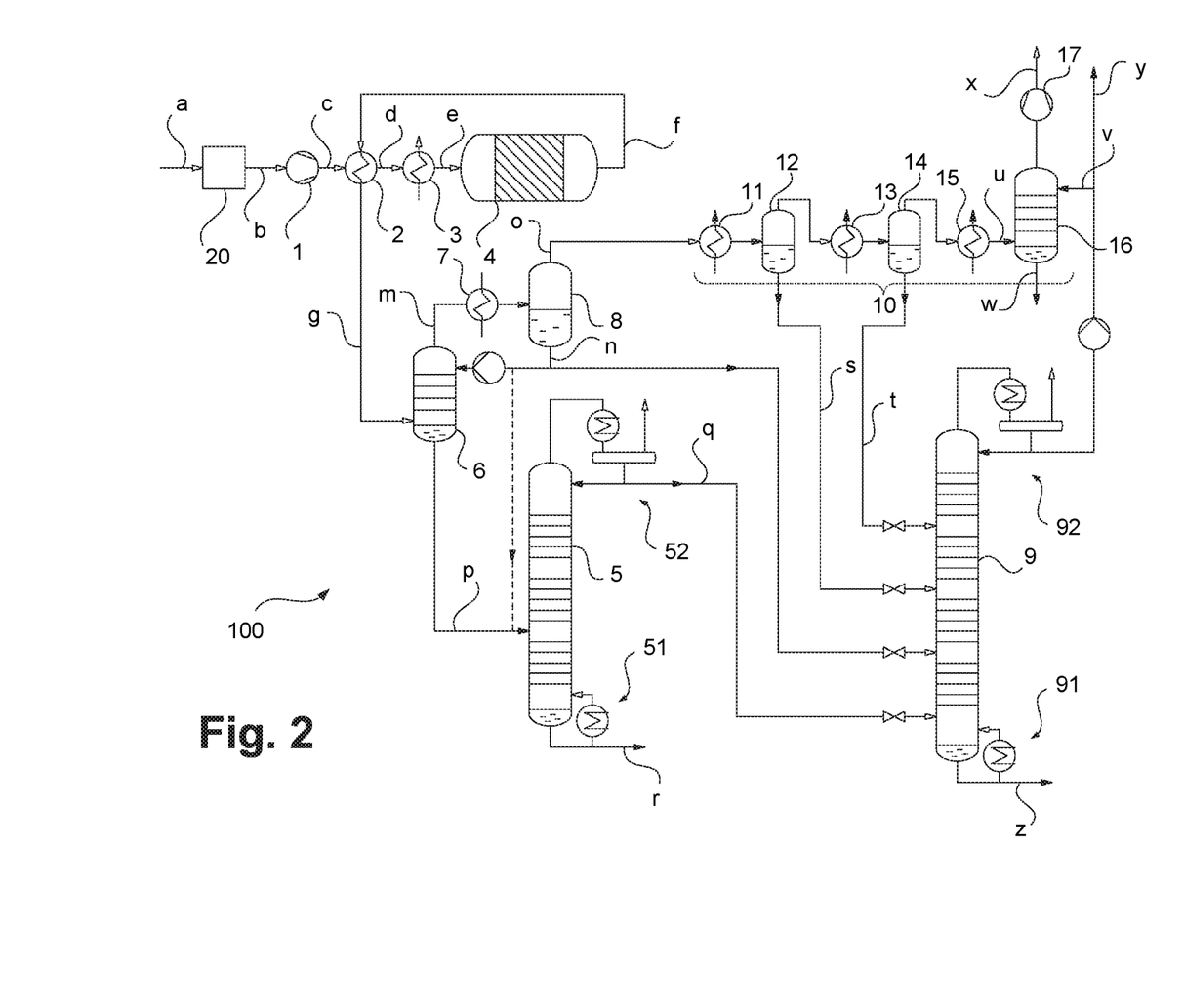
FIG. 2 shows an apparatus for the production of dimethyl ether according to an embodiment of the invention, in schematic representation.

This is illustrated in FIG. 2, which shows an apparatus for producing dimethyl ether according to one embodiment of the invention. This is generally designated 100.

The absorption column is designated 6 in FIG. 2. As already explained, an absorption column 6 differs from a distillation column such as the distillation columns 5 and 9 described hereinafter in that it does not have a sump evaporator, among other things. Vapours rising in the absorption column 6 are washed by a reflux added at the top of the absorption column, so that the more volatile components become concentrated at the top of the absorption column and the less volatile components become concentrated at the bottom of the absorption column.

In the apparatus 100 which is shown in FIG. 2, the stream g is piped into the absorption column 6. From the top of the absorption column 6 a top stream m is removed and cooled in a heat exchanger 7 against a suitable refrigerant, for example cooling water. The correspondingly cooled stream m is transferred into a separating container 8, from the bottom of which a liquid stream n is drawn off and added to the absorption column 6 by means of a pump (not shown) at least partly as a reflux.

If, besides dimethyl ether, the stream g in the embodiment shown contains methanol, water, carbon dioxide, carbon monoxide and hydrogen (as well as traces of other compounds as explained above), of these, dimethyl ether, carbon dioxide, carbon monoxide and hydrogen predominantly pass into the top stream m as a result of the backwash described above. As a result of suitable cooling in the heat exchanger 7 and corresponding separating conditions in the separating container 8, a sump product is separated off in the separating container 8 which consists essentially of dimethyl ether and carbon dioxide (optionally with traces of methanol).

From the top of the separating container 8, a stream o can be drawn off in gaseous form, also containing dimethyl ether, in addition to carbon dioxide, carbon monoxide and hydrogen. The stream o is then subjected to sequential cooling and condensation, as explained hereinafter. The fraction of the stream n which is not added to the absorption column 6 as liquid reflux can be fed into a distillation column 9 ("further distillation column") as in the sequential cooling and condensation of the steam o. Otherwise, it is fed into a distillation column 5 ("first distillation column") as indicated by a dashed arrow. A liquid stream p is drawn off from the bottom of the absorption column 6 and transferred into the distillation column 5.

The reflux quantity and number of plates in the absorption column 6 can be optimised so as to obtain a corresponding sump product p in a smaller amount. Advantageously, the reflux which is added to the absorption column 6 is adjusted so that the content of methanol and water in the stream m is minimised. The composition of the stream o thus produced is such that in the cooling and condensation sequence 10 to which the stream o is subjected the disadvantages described above, for example the freezing out of water, cannot arise.

In the distillation column 5 which is operated with a sump evaporator 51 and a top condenser 52, the stream p, which still consists essentially of methanol, hydrogen, dimethyl ether and carbon dioxide, is separated into a top stream consisting essentially of dimethyl ether and carbon dioxide and a sump stream r consisting essentially of methanol and/or water. Some of the top stream is liquefied in the top condenser 52 and added to the distillation column 5 as a reflux. Another liquefied fraction of the top stream is drawn off as the stream q, in the embodiment shown. The non-liquefied residue is taken for combustion, for example, in the embodiment shown. The stream q is referred to as the "transfer stream" within the scope of this application and transferred into a further distillation column 9. As already mentioned, unlike in the representation in FIG. 2, a transfer stream corresponding to the stream q may also be provided in gaseous form, particularly if the first distillation column 5 is operated at a higher pressure level than the further distillation column 9 described hereinafter. If the stream q is provided in liquid form and the operating pressure of the first distillation column 5 is below that of the further distillation column 9, a pump is used to increase the pressure. In the opposite case, pressure is released, for example, through a valve, as shown in FIG. 2. Non-liquefied fluid in the top condenser 5, the amount of which is advantageously minimised when producing a liquid transfer stream q, can also, instead of being utilised thermally, be partly recycled into the separation process at another suitable point, for which purpose it may optionally be compressed. The method of forming the transfer stream q is not limited to the embodiment shown here. For example, the stream q can also be transferred from the distillation column 5 into the distillation column 9 directly, i.e. circumventing the top condenser 52. The sump stream r can also be used at a suitable point. Any water separated off can be taken off for waste water treatment or for degassing.

The steps for further treatment of the stream o which have already been mentioned several times are generally designated 10 here. The stream o is first supplied to a heat exchanger 11 and then fed into a separating container 12. Cooling in the heat exchanger 11 is carried out so that a condensate s is separated off in the separating container 12. A fraction remaining in gaseous form in the separating container 12 is supplied to a heat exchanger 13 and then fed into another separating container 14. Here, too, a condensate is obtained, which is designated t.

The condensates s and t, together with the fraction of the stream n which is not recycled into the absorption column 6, are fed into the further distillation column 9 mentioned previously, which is operated as explained hereinafter. A fraction remaining in gaseous form at the top of the separating container 14 is cooled in another heat exchanger 15. It is located downstream of this heat exchanger 15, for example, at a temperature of −35° C. or below, for example, just above the melting temperature of carbon dioxide. The temperature of the stream o upstream of the heat exchanger 11, by contrast, is +35° C., for example. The correspondingly cooled stream, here designated u, is transferred into a further absorption column 16 in the embodiment shown. This is optional.

The stream u still contains dimethyl ether, carbon dioxide, carbon monoxide and hydrogen. Using a liquid reflux v which is formed from part of a condensate that is obtained from a top stream of the further distillation column 9, a mixture of dimethyl ether and carbon dioxide is separated off in the sump of the absorption column 16, in the embodiment shown. At the top of the absorption column 16, by contrast, a mixture is drawn off which consists essentially of carbon dioxide, carbon monoxide and hydrogen. This may be used for other purposes as stream x, optionally after being suitably compressed in a compressor 17. The use of the further absorption column 16 is optional; the stream u may also be processed in some other way.

The streams s and t and the transfer stream q are fed into the further distillation column 9. As they contain different amounts of dimethyl ether and carbon dioxide (traces of carbon monoxide and hydrogen are also present in dissolved form) they are fed into the distillation column 9 at different heights, for which purpose suitable valves (not designated) are provided. In the embodiment shown, the fraction of the stream n which is not recycled into the absorption column 6 is also fed into the further distillation column q. As already mentioned this is possible if this stream is free from water and optionally methanol. Alternatively, it is also possible to feed it into the first distillation column 5, as indicated by a dashed arrow.

The further distillation column 9 is also operated with a sump evaporator 91 and a top condenser 92. A top stream of the further distillation column 9 is at least partially liquefied in the top condenser 92 using a heat exchanger operated with a suitable refrigerant and is added to the further distillation column 9 as a liquid reflux. A further fraction is used to form the stream v and another stream y.

A liquid stream z which still consists essentially of dimethyl ether but is, in particular, free from or poor in carbon dioxide is removed from the sump of the further distillation column 9.

The invention claimed is:

1. Method for the processing, by separation technology, of a product stream (g) containing at least dimethyl ether, methanol, water, carbon dioxide, carbon monoxide and hydrogen, from a reactor (4) used for the synthesis of dimethyl ether from synthesis gas (e), comprising feeding the product stream (g), in at least partially gaseous form, into an absorption column (6) operated with a liquid reflux, removing a gaseous top stream (m) from the absorption column (6) at the top and removing a liquid sump stream (p) at the bottom, feeding the sump stream (p) at least partially into a first distillation column (5), withdrawing a transfer stream (q) containing dimethyl ether and a stream (r) predominantly containing methanol and/or water from the first distillation column (5), cooling the top stream (m) at least partially initially to a first temperature level and subsequently further cooling to one or more further temperature levels, forming a first condensate stream (n) after the cooling to the first temperature level and forming one or more further condensate streams (s, t) after the further cooling to the further temperature level or levels, and using the first condensate stream (n) partially to form the liquid reflux and feeding the further condensate stream or streams (s, t) at least partially into a further distillation column (9), from which removing a liquid stream (z) predominantly containing dimethyl ether and poor in or free from carbon dioxide at the bottom.

2. Method according to claim 1, further comprising feeding a fraction of the first condensate stream (n) which is not used to form the liquid reflux at least partially into the first distillation column (5) or the further distillation column (9).

3. Method according to claim 1, further comprising operating the absorption column (6) such that the top stream (m) is poor in methanol and/or water.

4. Method according to claim 1, further comprising selecting the further temperature level or levels such that the further condensate stream or streams (s, t) is or are poor in carbon monoxide and hydrogen.

5. Method according to claim 1, further comprising removing a gaseous top stream which is rich in carbon dioxide and poor in dimethyl ether from the further distillation column (9) at the top.

6. Method according to claim 1, further comprising feeding the product stream (g) into the absorption column (6) at a pressure level of 20 to 100 bar.

7. Method according to claim 1, further comprising feeding the product stream (g) into the absorption column (6) at a temperature level of 60 to 150° C.

8. Method according to claim 1, wherein the further cooling of the top stream (m) to the further temperature level or levels comprises cooling to a minimum temperature level between the melting temperature of carbon dioxide and −15° C.

9. Method according to claim 8, further comprising feeding a fraction of the top stream (m) which has remained in gaseous form after cooling to the minimum temperature level into a further absorption column (16).

10. Method according to claim 9, further comprising operating the further absorption column (16) with a further liquid reflux (v) which is formed from a liquefied, carbon dioxide-rich top stream from the further distillation column (9).

11. Method according to claim 1, wherein the product stream (g) contains 2 to 50 mol % dimethyl ether, 0.1 to 20 mol % methanol, 0.1 to 20 mol % water, 1 to 50 mol % carbon dioxide, 0.1 to 25 mol % carbon monoxide and 5 to 90 mol % hydrogen.

* * * * *